United States Patent
Zecha, Jr. et al.

(10) Patent No.: US 6,824,531 B1
(45) Date of Patent: Nov. 30, 2004

(54) MEDICAMENT CONTAINER WITH NEEDLE PROTECTION HOUSING

(75) Inventors: Frederick P. Zecha, Jr., Keene, NH (US); Louis Woo, Alexandria, VA (US)

(73) Assignee: Smiths Medical ASD, Inc., Keene, NH (US)

(*) Notice: Subject to any disclaimer, the term of this patent is extended or adjusted under 35 U.S.C. 154(b) by 0 days.

(21) Appl. No.: 10/617,704

(22) Filed: Jul. 14, 2003

(51) Int. Cl.[7] ............................................. A61M 5/32
(52) U.S. Cl. ................................. 604/192; 604/110
(58) Field of Search .................... 604/110, 164.08, 604/192, 187, 197, 198, 263

(56) References Cited

U.S. PATENT DOCUMENTS

| | | | | |
|---|---|---|---|---|
| 4,982,842 A | * | 1/1991 | Hollister | 206/365 |
| 5,011,475 A | * | 4/1991 | Olson | 604/192 |
| 5,232,454 A | * | 8/1993 | Hollister | 604/192 |
| 5,312,369 A | * | 5/1994 | Arcusin et al. | 604/192 |
| 5,405,332 A | * | 4/1995 | Opalek | 604/192 |
| 5,529,189 A | * | 6/1996 | Feldschuh | 206/570 |
| 5,564,565 A | * | 10/1996 | Yamada | 206/365 |
| RE37,110 E | * | 3/2001 | Hollister | 206/365 |
| 6,334,857 B1 | | 1/2002 | Hollister | |
| 6,524,281 B1 | | 2/2003 | Hudon | |
| 6,551,287 B2 | | 4/2003 | Hollister | |
| 2003/0060773 A1 | * | 3/2003 | Nguyen | 604/192 |

OTHER PUBLICATIONS

US Patent Applicant No. 09/962,240, filed Sep. 26, 2001.*

* cited by examiner

*Primary Examiner*—Sharon Kennedy
(74) *Attorney, Agent, or Firm*—Louis Woo

(57) ABSTRACT

A needle protective housing is fitted to the neck of a medicament container, for example a glass vial, that has a circumferential notch formed at a proximal portion of the neck. The needle protective device has a needle protective housing pivotally connected to a cup-shaped collar. The collar has a base that is formed by a plurality of coplanar extensions, that in turn form an aperture that allows the base to be press-fitted onto the neck of the vial. The extensions are each separated by a space, so that the extensions would give way when the collar is slidedly fitted along the length of the neck of the vial, until the extensions reach the notch at the proximal end of the neck of the vial where the extensions return to the original shape to thereby couple the collar to the vial. The circular wall upraised from the base of the collar is internally threaded for accepting the luer of a needle assembly, when the needle assembly is mated to the neck of the syringe. Once fully threaded into the collar, the interaction of the luer and the base of the collar effects a tightly gripped fit of the base about the neck of the collar. Once the housing is pivoted to cover a contaminated needle, a lock mechanism at the housing would fixedly retain the needle. Once retained, the contaminated needle will continue to be retained within the housing even in the unlikely event that the collar and needle protective housing are forcibly removed from the vial.

20 Claims, 3 Drawing Sheets

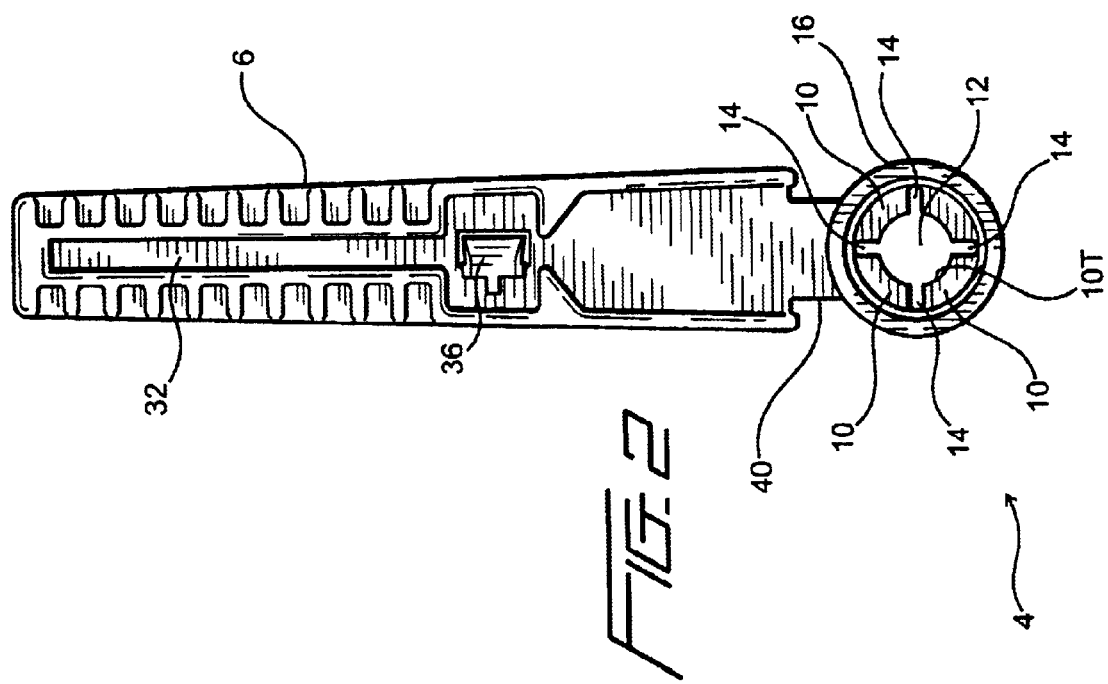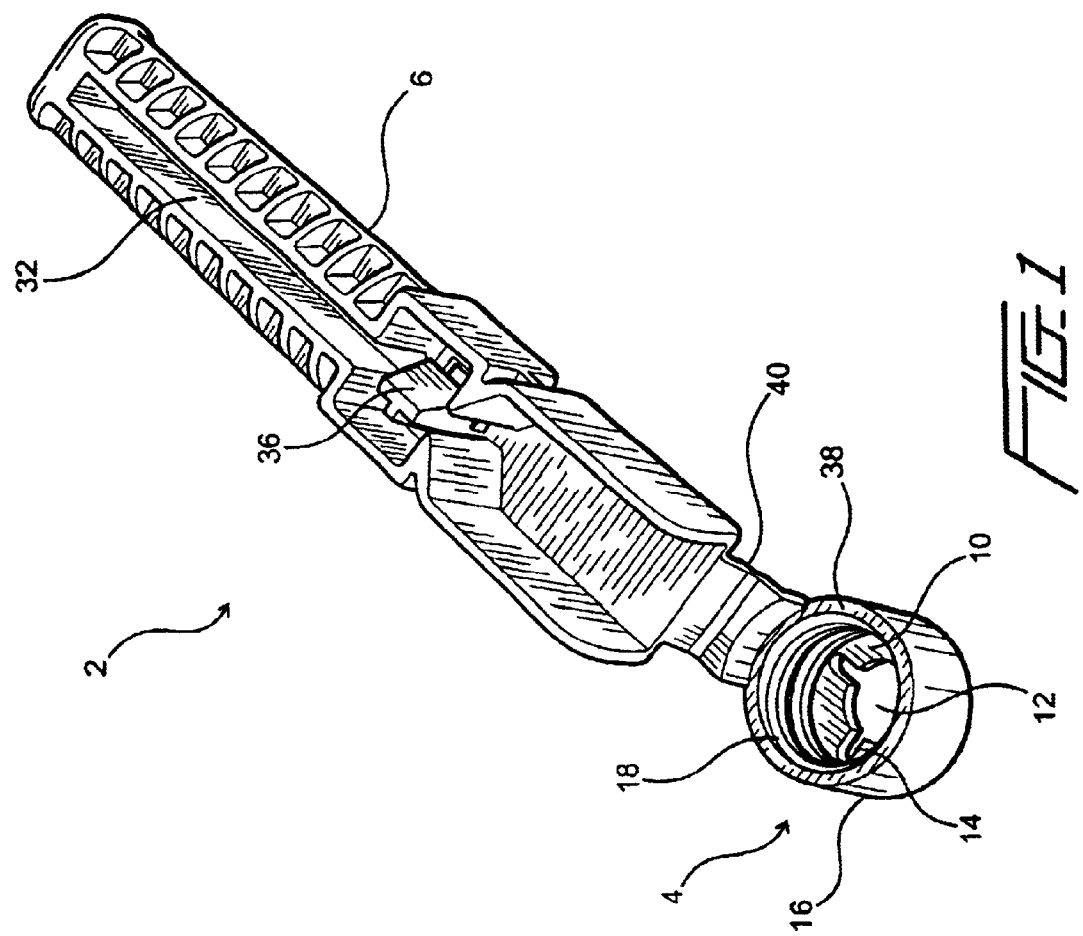

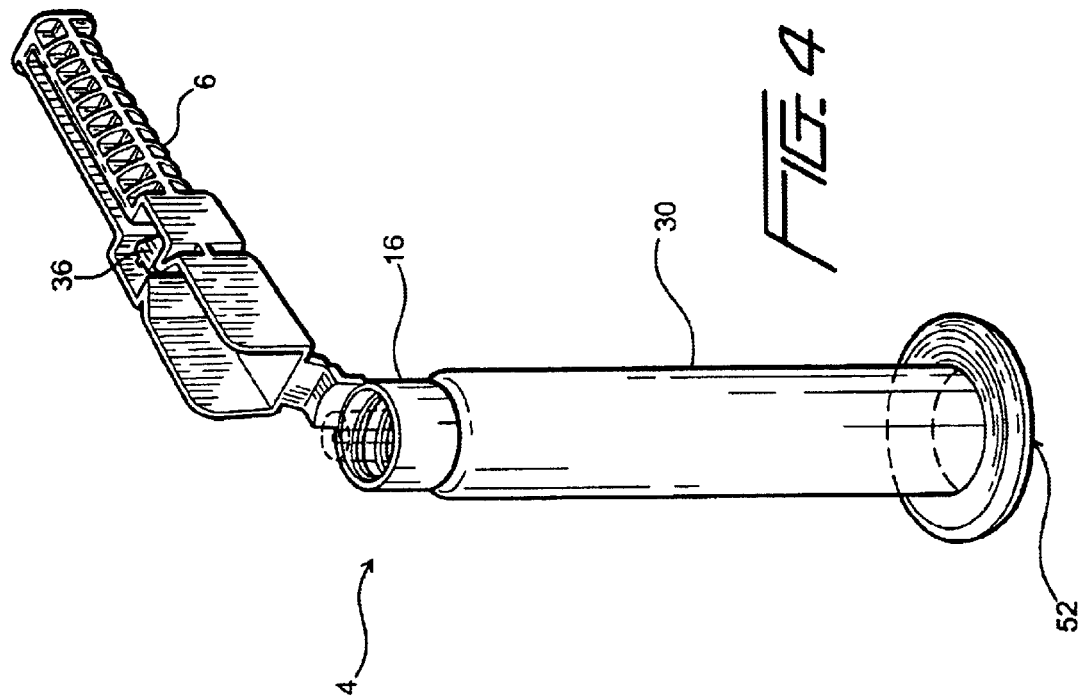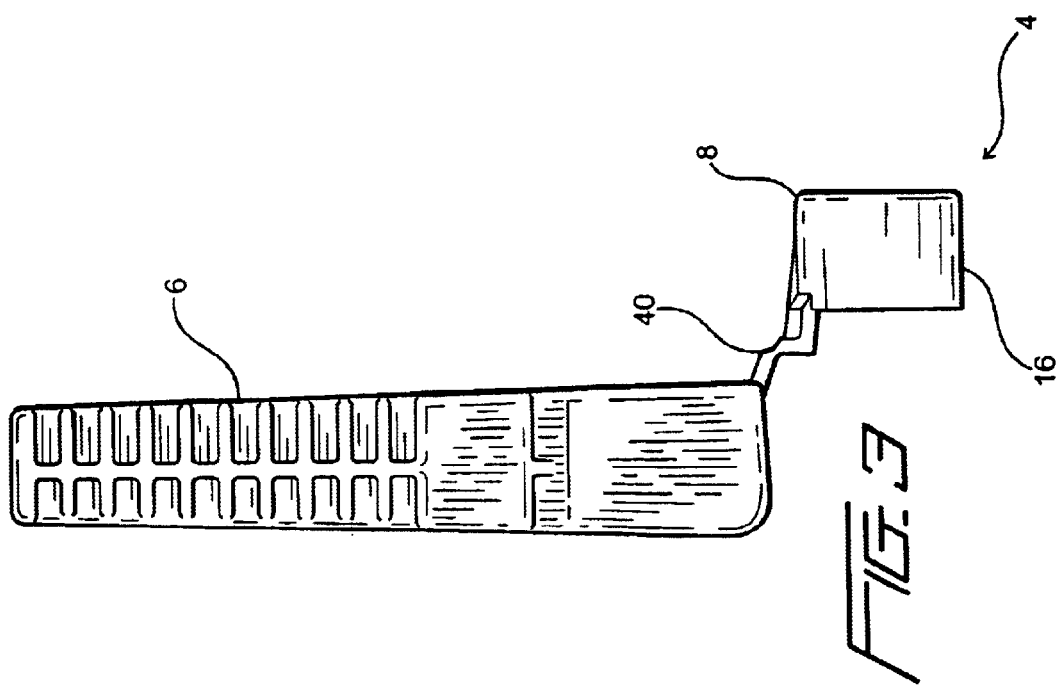

MEDICAMENT CONTAINER WITH NEEDLE PROTECTION HOUSING

FIELD OF THE INVENTION

The present invention relates to needle protective devices and particularly to a medicament container such as for example a glass vial that has fitted thereto a housing that covers a needle after use.

SUMMARY OF THE PRESENT INVENTION

The assignee of the instant invention has under assignment the following U.S. patents all of which deal with vials having needle protection housings: U.S. Pat. No. 6,334,857; U.S. Pat. No. 6,524,281; and U.S. Pat. No. 6,551,287. The respective disclosures of the '857, '281 and '287 patents are incorporated by reference to the instant disclosure. The vials disclosed in the above-noted patents are vials that are used with different injection applicators.

The instant invention is directed to providing a needle protection housing to a vial and slip syringe, glass or otherwise, that has a neck extending from a longitudinal body, and to which neck is mated a conventional needle having a luer end.

The glass vial or slip fit syringe for the instant invention has formed at its neck, at its proximal portion, an undercut in the form of a circumferential notch. A collar that is cup-shaped has as its bottom base a plurality of extensions that converge toward, but not touching, the center of the base so as to form a central aperture at the base. The extensions are separated by spaces so that when the collar, with the base first, is slidably fitted over the neck of the vial, the coplanar extensions would give way, when in contact with the neck of the vial, to effect a smooth sliding motion until the extensions reach the circumferential notch. At which time the extensions would return to their original shape to thereby firmly couple the collar to the base, with the converging ends of the extension mated to the circumferential notch of the neck of the vial.

The collar has a circular sleeve rising from the base. The inner wall of the upraised sleeve is threaded, and is configured to threadingly mate with a luer end of a conventional needle that fits to the neck of the vial. The internal thread of the sleeve may be configured as a one way thread so that once the luer of the needle is fully mated to the collar, it could no longer be removed therefrom. Also, once the collar is properly fitted to the neck of the vial, with the base mated to the circumferential notch, when the luer of a needle is fully mated to the collar, the extensions that made up the base would be pulled upwards by the luer end of the needle to firmly couple the base to the top undercut portion of the circumferential notch.

A needle protection housing is flexibly connected to the collar, possibly at a portion of the upper lip of the sleeve that extends toward the distal end of the neck of the vial. The housing has a longitudinal slot through which a needle that is mated to the neck of the vial passes when the housing is pivoted toward the needle for covering the needle. A lock mechanism, in the form of a hook, is integrated to the inside of the housing for grasping and retaining the needle after use, when the housing is pivoted to the alignment position to cover the needle. Given that the luer end is threaded to the collar, even were the collar forcibly removed from the neck or the vial breaks, the contaminated needle would continued to be retained inside the housing.

BRIEF DESCRIPTION OF THE FIGURES

The instant invention will become apparent and will be best understood by reference to the following description of the invention taken in conjunction with the accompanying drawings, wherein:

FIG. 1 is a perspective view of the needle protection housing and the inventive collar to which it is attached;

FIG. 2 is a top view of the FIG. 1 needle protective device;

FIG. 3 is a side view of the FIG. 1 needle protection device;

FIG. 4 is a perspective view of the needle protection device of the previous figures shown to be mated to a vial;

DETAILED DESCRIPTION OF THE INVENTION

Figure 6:
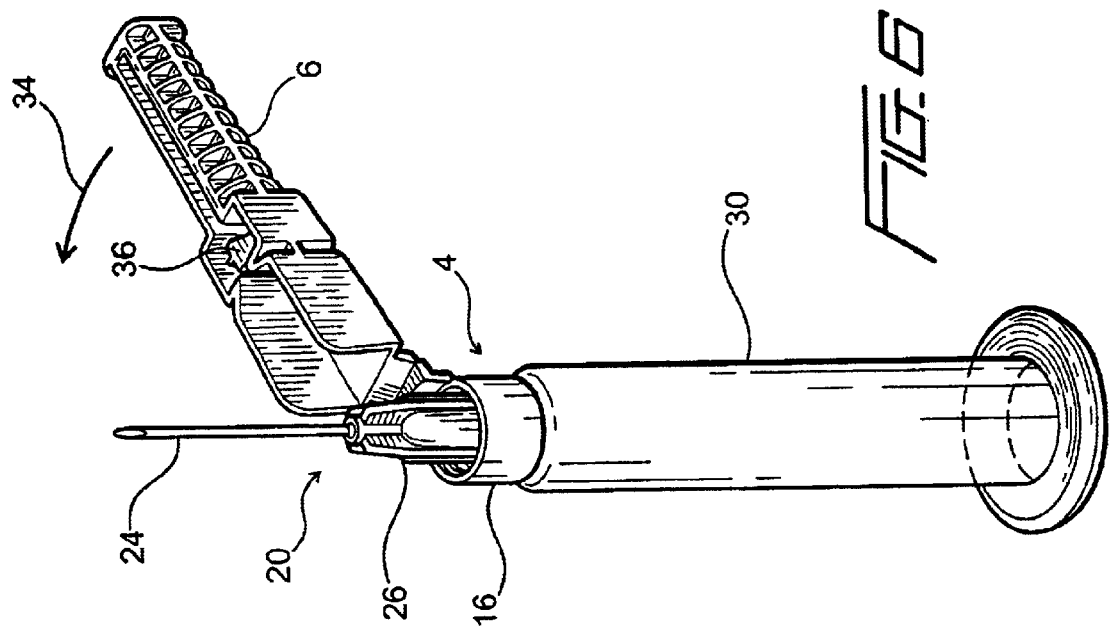
FIG. 6 is a perspective view showing the vial of FIG. 4 fitted with a needle.

With reference to the figures, the needle protective device 2 of the instant invention is shown to comprise a collar 4 and a needle protective housing 6. In particular, collar 4 has a base 8 which is formed by a plurality of converging, although not touching, planar extensions 10. Each of the extensions 10 is configured such that, in combination, they form an aperture 12 that is defined by the respective front edges or tips 10t of the extensions. A plurality of spaces or slots 14 each separate an adjacent pair of extensions 10. Because of spaces 14 and the characteristics of the plastic materials such as polypropylene from which collar 4, as well as housing 6, is molded, extensions 10 each tend to have a given elasticity and will give way when base 8 of collar 4 is fitted about, and the extensions in contact with, an elongate object such as for instance the neck 28 of the vial 30 as shown in FIGS. 4 and 5.

Extending upwards or rising from base 8 of collar 4 is a circular wall or sleeve 16, thereby giving the collar a cup-shaped look. The inner wall of sleeve 16 is formed with a spiraling groove 18 that allows the threaded mating of collar 4 to a luer end, such as 22 of the needle assembly 20 shown in FIGS. 5 and 6. Note that needle assembly 20 is conventional in that a needle 24 extends from a needle hub 26, which has luer end 22 and an open end for mating with neck 28 of a medicament container such as vial 30.

Housing 6 is shown to have an elongate slot 32 that allows needle 24 to pass when housing 6 is pivoted in the direction, as designated by directional arrow 34, toward needle 24, per shown in FIG. 6. A lock mechanism in the form of a hook 36 is integrated to housing 6 for grasping and retaining needle 24, when housing 6 has been pivoted to a position that extends substantially along the longitudinal axis of vial 30 for covering needle 24. Once grasped by hook 36, needle assembly 20 is retained within housing 6, even when collar 6 and needle hub 26 were forcibly removed from vial 30 or if vial 30 were to break. Housing 6 is flexible connected to collar 4 by means of a living hinge 40. As shown in FIG. 1, living hinge 40 is connected to the lip 38 of upraised sleeve 16.

Figure 5:
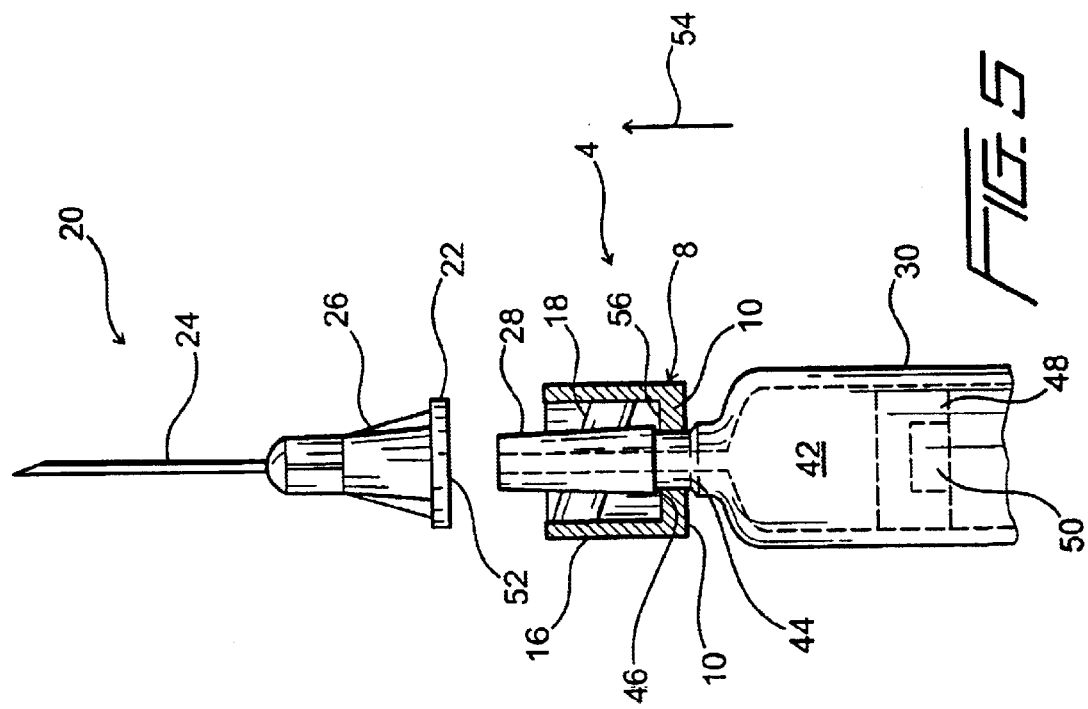
FIG. 5 is a cut-away view of the instant invention showing the mating of the collar to the neck of a vial.

With reference to FIGS. 4–6, collar 4 is shown to have been press-fitted, or mated to neck 28 of a medicament container vial 30, which may be a glass vial. As best shown in FIG. 5, vial 30 has extending from its one end neck 28 which establishes a fluid communication path between the interior chamber 42 of vial 30 and the outside environment. A circumferential notch 44 is formed at the proximal portion of neck 28. An undercut 46 is defined circumferentially by the upper end of notch 44.

When collar 4 is press-fitted onto neck 28 for installing the needle protective device to vial 30, aperture 12, which is formed by the plurality of converging extensions 10 at base 8 of collar 4, is slidably fitted about neck 28. Due to their elastic nature enhanced by the plurality of spaces 14 formed between adjacent pairs of extensions 10, aperture 12 would expand, or alternatively speaking extensions 10 will give way, so that collar 4 is readily slidable over neck 28, until the extensions 10 reach notch 44 and become snap fitted thereto. At which time extensions 10 would return to their original shape. As a consequence, since aperture 12 has a smaller diameter than the circumference defined by undercut 44, collar 4 is substantially fixedly coupled to neck 28 of vial 30.

A rubber gasket 48 is fitted into and slidable along the length of the interior of the vial. A coupling void 50 is provided at the end of gasket 48 that faces the open end 52 of vial 30. Although not shown, a plunger may be inserted into vial 30 so that its head mates with void 50 of gasket 48 to thereby enable the plunger to move gasket 48 to control the ejection of the medicament stored in chamber 42 of vial 30.

Once collar 4 is properly fitted about neck 26, with extensions 10 fitted about notch 44, needle assembly 20 may be connected to vial 30 with an opening 52 of needle hub 26 mating with neck 28 while luer end 22 threadingly mating with groove 18 at the inner wall of sleeve 16. Groove 18 is designed such that when needle assembly 20 is fully threaded into collar 4, due to the interaction of luer 22 and groove 18, base 8, or more precisely extensions 10 thereof, are pulled in the direction as indicated by directional arrow 54, so that surface 56 of base 8 is firmly held by the circumferential undercut 46. As a consequence, the needle protective housing 2 is firmly coupled to neck 28 of vial 30. After use, needle 24 is covered by housing 6 when housing 6 is pivoted along the direction indicated by directional arrow 34. Needle 24 is retained within the interior of housing 6 by hook 36. The used vial including the retained contaminated needle could then be discarded.

Given that needle 24 is retained within housing 6 and the luer end 22 is threadingly mated to collar 4, needle assembly 20 is therefore fixedly coupled to the needle protection device as shown in FIGS. 1–3. Accordingly, even if someone were to deliberately and forcibly remove collar 4 from neck 38 of vial 30, needle assembly 20 nonetheless will remain fixed to the needle protection device and the contaminated needle 24 covered by housing 6.

In place of firmly coupling collar 4 to neck 28, housing 16 of collar 8 may be configured to have a one-way groove 18 so that, once luer end 22 of needle assembly 20 is fully threaded into collar 4, it could not be removed even by a reverse rotational movement, as groove 8 forms a one-way thread. Accordingly, once needle assembly 20 is fully threaded into collar 4, it will remain coupled to collar 4, and to neck 28 of vial 30, during usage as well as when the vial is discarded after usage.

So, too, if it is desirable to have housing 6 rotatable about needle 24, a space may be provided just above the coplanar extensions in sleeve 16, so that once luer end 22 is fully threaded into collar 4, it will rest within the space while at the same time being slip fitted to neck 28. As a result, collar 4 is rotatable about needle 24, and yet needle assembly 20 is not removable from collar 4. Once used, needle 24 is covered by housing 6 as discussed above, and the contaminated needle 24, protected by housing 6, is discarded along with vial 30.

Note that although a vial is disclosed as being the medicament container throughout the disclosure, it should be appreciated that a syringe that has a neck similar to that disclosed may also be fitted with the needle protective device of the instant invention. Moreover, instead of a hook, the lock mechanism for the inventive needle protection device may comprise a first lock portion at base 4 and a second lock portion that coacts with the first lock portion at the lower portion of housing 6, per disclosed in U.S. Patent RE 37,110, for fixedly locking housing 6 to base 4. The disclosure of the '110 patent is incorporated by reference to the instant disclosure.

What is claimed is:

1. Apparatus comprising: a vial, said vial having a neck for receiving a needle, said neck configured to include a circumferential notch, a needle protection housing coupled to said neck via a collar, said needle protection housing pivotable to be in alignment along the longitudinal axis of said vial, said collar including a base configured to be press fitted onto said neck.

2. Apparatus of claim 1, wherein said base of said collar comprises an aperture formed by a plurality of converging planar extensions, adjacent pairs of said extensions at least partially separated by a space to allow said extensions to give way to enable said collar to slide along said neck when said collar is being press fitted onto said neck until said extensions reach said notch, said collar further comprising a circumferential sleeve rising from said base, the inner wall of said sleeve being threaded to accept a luer of said needle when said needle is mated to said neck of said vial.

3. Apparatus of claim 2, wherein said base of said collar is tightly coupled to said neck of said vial when the luer of said needle is fully threaded to said collar, said needle remaining threaded to said collar after said vial is used.

4. Apparatus of claim 2, wherein the inner wall of said sleeve is configured to be threaded only one way so that once fully threaded into said collar, the luer of said needle is prevented from being removed from said collar.

5. Apparatus of claim 1, wherein said vial is made of glass, said vial having an open end and a channel extending along said neck, a rubber gasket being provided inside said vial to partition the inside of said vial from the open end, said gasket movable along the interior of said glass vial to drive fluid stored therein through said channel to said needle, said gasket having a receptacle at its end facing the open end of said vial for accepting a plunger.

6. Apparatus of claim 1, wherein said housing comprises an integral needle grasping means for fixedly retaining the needle when said housing is pivoted to be in alignment along the longitudinal axis of said vial.

7. A needle protective device adapted to be used with a medicament container, comprising: an elongate housing having a longitudinal opening through which a needle attached to a neck of said medicament container passes when said housing is pivoted toward the needle, said housing pivotally connected to a collar, said collar being cup-shaped with a base having an aperture fitted to said neck of said medicament container, said aperture being formed from a plurality of planar extensions that mate to a notch circumferentially formed on said neck, said collar having a circumferential sleeve upraised from said base, the inner wall of said sleeve internally threaded for mating with a luer of the needle when the needle is mated to said neck, said housing pivotally connected to said collar, a locking mechanism at at least said housing for fixedly retaining said needle relative to said housing after said needle passes into said housing.

8. Needle protective device of claim 7, wherein adjacent ones of said extensions of said base of said collar are separated by spaces to allow said extensions to give way when said collar is slidably fitted onto said neck, said extensions returning to their original shape once said extensions are seated at said notch, said collar remaining substantially fixed to said neck once said base is fitted about said notch of said neck.

9. Needle protection device of claim 7, wherein said medicament container comprises a glass vial having an open end, a rubber gasket being provided inside said vial to partition the inside of said vial from the open end, said gasket movable along the interior of said glass vial to control the flow of fluid to and from said container, said gasket having a receptacle at its end facing the open end of said vial for accepting a plunger for controlling the movement of said gasket in said vial.

10. Needle protection device of claim 7, wherein said medicament container comprises a syringe.

11. Needle protection device of claim 7, wherein said lock mechanism comprises a first portion at said collar and a second portion coactable with said first portion at said housing, said first and second portions coact to prevent said housing from being removed from said collar once said housing is pivoted toward and covers said needle.

12. A method of providing a needle protection housing to a medicament container having a neck at one end and an opening at another end, comprising the steps of:
   a) forming a circumferential notch around said neck of said container;
   b) forming a collar having a base including a central aperture formed by a plurality of converging planar extensions;
   c) extending upwards from said base an internally threaded circumferential sleeve as part of said collar;
   d) pivotally connecting, a needle protection housing to said collar; and
   e) press fitting said collar to said neck of said container until said extensions of said base fit about said notch;
   wherein when a needle having a luer end is mated to said neck of said container, said lure end is threadingly mated to said sleeve of said collar.

13. Method of claim 12, further comprising the steps of:
   forming an opening longitudinally along said housing to allow said needle mated to said neck of said container to pass through when said housing is pivoted toward said needle; and
   integrating a lock mechanism to said housing for fixedly retaining said needle when said housing is pivoted to cover said needle.

14. Method of claim 12, wherein said step b further comprising the step of:
   separating adjacent pairs of said extensions at least partially by a space to allow said extensions to give way to enable said base via its aperture to slide along said neck when said collar is being press fitted onto said neck of said container until said extensions reach said notch, said extensions tightly coupling said collar to said neck when said needle is threadingly mated to said collar.

15. Method of claim 12, wherein said step b further comprising the step of:
   providing a one way thread to the inner circumferential wall of said sleeve so that once the luer end of said needle is fully threaded to said collar, said needle is not removable from said collar.

16. In combination, a medicament container having a neck with a circumferential notch formed at a proximal end thereof, a fluid communication path being established between the inside of said container and the environment through said neck, a cup-shaped collar having a base with an aperture formed by a plurality of converging extensions fitted about said notch of said neck, a circular sleeve rising from said base with the lip of said sleeve pointing toward the distal end of said neck, the inner wall of said sleeve being threaded to receive a luer end of a needle when said needle is mated to said neck, a housing connected to said base and pivotable to a position in alignment along the longitudinal axis of said container, said housing having an integral hook for grasping said needle when said housing is pivoted to the alignment position.

17. Combination of claim 16, wherein said base comprises a plurality of spaces each separating adjacent pairs of said converging extensions for enabling said base to be readily press fitted onto said neck, said base fitting tightly about said neck at said notch when said luer end of said needle is fully threaded into said collar.

18. Combination of claim 16, wherein the thread formed on the inner wall of said sleeve is configured to prevent said luer end from being removed from said collar once it is fully threaded into said collar.

19. Combination of claim 16, wherein said container comprises a glass vial.

20. Combination of claim 16, wherein said container comprises a syringe.

* * * * *